United States Patent
Niitsu et al.

(10) Patent No.: US 10,098,953 B2
(45) Date of Patent: *Oct. 16, 2018

(54) THERAPEUTIC AGENT FOR FIBROID LUNG

(71) Applicant: Nitto Denko Corporation, Osaka (JP)

(72) Inventors: Yoshiro Niitsu, Sapporo (JP); Rishu Takimoto, Sapporo (JP)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/883,370

(22) Filed: Oct. 14, 2015

(65) Prior Publication Data

US 2016/0030571 A1 Feb. 4, 2016

Related U.S. Application Data

(63) Continuation of application No. 13/867,346, filed on Apr. 22, 2013, which is a continuation of application No. 13/585,736, filed on Aug. 14, 2012, which is a continuation of application No. 12/933,075, filed as application No. PCT/JP2009/001148 on Mar. 16, 2009.

(30) Foreign Application Priority Data

Mar. 17, 2008 (JP) ................................. 2008-068227

(51) Int. Cl.
| | | |
|---|---|---|
| A61K 47/10 | (2017.01) | |
| A61K 31/713 | (2006.01) | |
| C12N 15/113 | (2010.01) | |
| A61K 9/127 | (2006.01) | |
| A61K 9/00 | (2006.01) | |
| A61K 31/7088 | (2006.01) | |
| C12N 15/11 | (2006.01) | |

(52) U.S. Cl.
CPC .............. A61K 47/10 (2013.01); A61K 9/007 (2013.01); A61K 9/127 (2013.01); A61K 31/7088 (2013.01); A61K 31/713 (2013.01); C12N 15/111 (2013.01); C12N 15/113 (2013.01); C12N 2310/11 (2013.01); C12N 2310/12 (2013.01); C12N 2310/14 (2013.01); C12N 2310/3515 (2013.01); C12N 2320/30 (2013.01); C12N 2320/32 (2013.01)

(58) Field of Classification Search
None
See application file for complete search history.

(56) References Cited

U.S. PATENT DOCUMENTS

| | | | |
|---|---|---|---|
| 4,966,773 A | 10/1990 | Gressel et al. | |
| 5,643,584 A | 7/1997 | Farng et al. | |
| 5,811,119 A | 9/1998 | Mehta et al. | |
| 5,851,538 A | 12/1998 | Froix et al. | |
| 6,183,774 B1 | 2/2001 | Aust et al. | |
| 8,178,124 B2 | 3/2012 | Niitsu et al. | |
| 8,173,170 B2 | 5/2012 | Niitsu et al. | |
| 8,574,623 B2 | 1/2013 | Niitsu et al. | |
| 8,652,526 B2 | 2/2014 | Niitsu et al. | |
| 8,686,052 B2 | 4/2014 | Niitsu et al. | |
| 2002/0012998 A1 | 1/2002 | Gonda et al. | |
| 2003/0064094 A1 | 4/2003 | Frankenberger et al. | |
| 2003/0096739 A1 | 5/2003 | Morris | |
| 2003/0161791 A1 | 8/2003 | Bentley et al. | |
| 2003/0211143 A1 | 11/2003 | Liu et al. | |
| 2004/0028682 A1 | 2/2004 | Border et al. | |
| 2005/0004064 A1 | 1/2005 | Tei et al. | |
| 2005/0165227 A1 | 7/2005 | Vlahov et al. | |
| 2006/0013775 A1 | 1/2006 | Gristwood et al. | |
| 2006/0074041 A1 | 4/2006 | Johnston et al. | |
| 2008/0057030 A1 | 3/2008 | Crager | |
| 2008/0193512 A1 | 8/2008 | Niitsu et al. | |
| 2008/0279765 A1 | 11/2008 | Chettibi et al. | |
| 2009/0105179 A1 | 4/2009 | Yu et al. | |
| 2010/0028416 A1 | 2/2010 | Yu et al. | |
| 2010/0144659 A1 | 6/2010 | Niitsu et al. | |
| 2011/0104255 A1 | 5/2011 | Niitsu et al. | |
| 2011/0178157 A1 | 7/2011 | Jin et al. | |
| 2011/0229558 A1 | 9/2011 | Niitsu et al. | |
| 2012/0269886 A1 | 10/2012 | Niitsu et al. | |
| 2012/0328694 A1 | 12/2012 | Niitsu et al. | |
| 2013/0011336 A1 | 1/2013 | Niitsu et al. | |
| 2013/0045272 A1 | 2/2013 | Niitsu et al. | |
| 2013/0136789 A1 | 5/2013 | Niitsu et al. | |
| 2013/0171127 A1 | 7/2013 | Niitsu et al. | |
| 2013/0171240 A1 | 7/2013 | Niitsu et al. | |
| 2013/0172401 A1 | 7/2013 | Niitsu et al. | |

(Continued)

FOREIGN PATENT DOCUMENTS

| | | |
|---|---|---|
| CN | 101102795 A | 1/2008 |
| CN | 101102795 A | 1/2008 |

(Continued)

OTHER PUBLICATIONS

Scherer et al., Nature Biotech. 2003, 21(12)1457-1465.*
Ueda et al., "Fibroblast cells and their associated cells [in Japanese]," Respiration Research, Jul. 1995, vol. 14. No. 7, p. 708-712.
Senoo et al., "Hepatic stellate cells and alveolar septa cells [in Japanese]," Respiration Research, 1997, vol. 16, No. 4, pp. 604-615.
Senoo, "Studies of the Vitamin A-Storing (Stellate) Cell system—From Molecules to the Arctic area [in Japanese]," [Bitamin] Vitamins, 2006, vol. 80, No. 3, pp. 105-113.
Andrew, E.R., et al., "Molecular motion in solid all-trans retinoic acid (vitamin A acid) by proton NMR." Solid State Nuclear Magnetic Resonance 13, pp. 39-43, 1998.

(Continued)

*Primary Examiner* — James D Schultz
(74) *Attorney, Agent, or Firm* — Knobbe, Martens, Olson & Bear, LLP (57) ABSTRACT

Disclosed are: a substance transfer carrier to an extracellular matrix-producing cell in the lung, which comprises a retinoid; a therapeutic agent for fibroid lung, which utilized the carrier; and a preparation kit of the therapeutic agent.

6 Claims, 6 Drawing Sheets

Specification includes a Sequence Listing.

(56) References Cited

U.S. PATENT DOCUMENTS

| | | |
|---|---|---|
| 2013/0210744 A1 | 8/2013 | Niitsu et al. |
| 2013/0216611 A1 | 8/2013 | Niitsu et al. |
| 2013/0267581 A1 | 10/2013 | Niitsu et al. |
| 2014/0127187 A1 | 5/2014 | Niitsu et al. |
| 2014/0315975 A1 | 10/2014 | Niitsu et al. |
| 2014/0323550 A1 | 10/2014 | Ayabe et al. |

FOREIGN PATENT DOCUMENTS

| | | |
|---|---|---|
| EP | 1842557 | 10/2007 |
| EP | 2135600 | 12/2009 |
| JP | 08-268906 | 10/1996 |
| JP | 11-269076 | 10/1999 |
| JP | 2002-047211 | 2/2002 |
| JP | 2002-363094 | 12/2002 |
| JP | 2002-371006 | 12/2002 |
| JP | 2003-119138 | 4/2003 |
| JP | 2003-219893 | 8/2003 |
| JP | A 2004-083436 | 3/2004 |
| JP | 2005-513031 | 5/2005 |
| JP | 2005-531628 | 10/2005 |
| JP | 2006-502153 | 1/2006 |
| JP | B 5517306 | 4/2014 |
| WO | WO 1991/004748 | 4/1991 |
| WO | WO 00/57913 | 10/2000 |
| WO | WO 2000/064478 | 11/2000 |
| WO | WO 01/68081 | 9/2001 |
| WO | WO 2001/1068081 | 9/2001 |
| WO | WO 02/083186 | 10/2002 |
| WO | WO 2003/009881 | 2/2003 |
| WO | WO 2003/045383 | 6/2003 |
| WO | WO 03/080594 | 10/2003 |
| WO | WO 2003/080594 | 10/2003 |
| WO | WO 2004/001381 | 12/2003 |
| WO | WO 2004/019921 | 3/2004 |
| WO | WO 2004/069159 | 8/2004 |
| WO | WO 2004/090108 | 10/2004 |
| WO | WO 2005/082402 | 9/2005 |
| WO | WO 2006/068232 | 6/2006 |
| WO | WO 2006/113679 A2 | 10/2006 |
| WO | WO 2008/120815 | 10/2008 |

OTHER PUBLICATIONS

Blomhoff et al., "Hepatic Uptake of [H] Retinol Bound to the Serum Retinol Binding Protein Involves Both Parenchymal and Perisinusoidal Stellate Cells," The Journal of Biological Chemistry 1985; 260(25): 13571-13575.

Blomhoff, Rune, et al., Newly Administered [$^3$ H] Retinol is Transferred from Hepatocytes to Stellate Cells in Liver for Storage. Experimental Cell Research, vol. 150, pp. 186-193, 1984.

Devi, GR. "siRNA-based Approaches in Cancer Therapy", Cancer Gene Therapy (2006) 13, 819-29.

Dixon et al., "Nomenclature of Retinoids." Pure & Appl. Chem., vol. 55, No. 4, pp. 721-726 (1983).

Dunham et al., Membrane fusion: Studies with a calcium-sensitive dye, arsenazo III, in liposomes. Proceedings of the National Academy of Science, USA, vol. 74, No. 4, pp. 1580-1584, 1997.

Fortuna V.A. et al., "Hepatic Stellate Cells Uptake of Retinol Associated With Retinol-Binding Protein or With Bovine Serum Albumin," Journal of Cellular Biochemistry 2003; 90(4):792-805.

Friedman, S. L., "Targeting siRNA to arrest fibrosis," Nature Biotechnology (Apr. 2008) 26(4): 399-400.

Goodman et al., "Extraction and Recombination Studies of the Interaction of Retinol with Human Plasma Retinol-Binding Protein." Journal of Lipid Research, vol. 13, 1972, pp. 338-347.

Kamps, J.AAM. et al., "Massive targeting of liposomes, surface-modified with anionized albumins, to hepatic endothelial cells," Proceedings of the National Academy of Sciences USA 1997; 94(21):11681-11685.

Kikuchi, H., Liposomes based on nanotechnology. Past, present and future. Part II, Pharm Tech Japan 2003; 19(3):419-433.

Kim et al., "Folate-tethered emulsion for the target delivery of retinoids to cancer cells." European Journal of Pharmaceutics and Biopharmaceutics. 68:618-625. (2008).

Li, D. et al., "Liver fibrogenesis and the role of hepatic stellate cells: New insights and prospects for therapy," Journal of Gastroenterology and Hepatology 1999; 14(7):618-633.

Lim et al., "Formulation parameters determining the physicochemical characteristics of solid lipid nanoparticles loaded with all-trans retinoic acid." International Journal of Pharmaceutics. 243:135-146. (2002).

Ma et al., "Comparison of Stability for All-trans Retinoic Acid Nanosuspensions and Lipid Nanoparticle Formulations." International Conference on Complex Medical Engineering. 197-202. (2007).

Sato et aL, Resolution of liver cirrhosis using vitamin A-coupled liposomes to deliver siRNA against a collagen-specific chaperone, Nature Biotechnology (2008) 26(4):431-442.

Selman et al, "Idiopathic Pulmonary Fibrosis: Prevailing and Evolving Hypotheses about It Pathogenesis and Implications for Therapy", Annal of Internal Medicince. Jan. 16, 2001, vol. 134, No. 2, pp. 136-151.

Singh, et al. "Liposome encapsulated vitamin A compounds exhibit greater stability and diminished toxicity." Biophysical Chemistry, vol. 73, pp. 155-162, 1998.

Socaciu, et al., Different Ways to Insert Carotenoids into Liposomes Affect Structure and Dynamics of the Bilayer Differently. Biophysical Chemistry, vol. 99, pp. 1-15, 2002.

Torchilin et al., "Immunomicelles: Targeted pharmaceutical carriers for poorly soluble drugs." PNAS. 100(10):6039-6044. (2003).

Torchilin, VP., "Targeted pharmaceutical nanocarriers for cancer therapy and imaging" The AAPS Journal (2007) 9(2):E128-47.

Tsuji, H. et al., "Targeting of liposomes surface-modified with glycyrrhizin to the liver. I. Preparation and biological disposition," Chemical & Pharmaceutical Bulletin 1991; 39(4):1004-08.

Vogel et al., "An immortalized rat liver stellate cell line (HSC-TS): a new cell model for the study of retinoid metabolism in vitro." Journal of Lipid Research, vol. 41, 2000, pp. 882-893.

Wassall, S.R., et al. "Retinoid-Phospholipid Interactions as Studied by Magnetic Resonance" Bulletin of Magnetic Resonance, vol. 9 No. 3, pp. 85-89, 1987.

Watanabe, et al., Treatment of idiopathic myelofiosis employing siRNA for heat shock protein 7 (siRNA/HSP47) encapsulated in liposomes, Blood (2007) 110:235.

Whitmer et al., Membrane-membrane interactions associated with rapid transfer of liposomal bilirubin to microsomal UDP-glucuronyltransferase. Biochemical Journal, vol. 244, pp. 41-47, 1987.

Wu, J. et al., "Modification of liposomes for liver targeting," Journal of Hepatology (1996)24(6):757-763.

Zhang et al., "Cationic lipids and polymers mediated vectors for delivery of siRNA," J. Control Release (2007) 123: 1-10.

Zhao et al.; "Tumor-selective targeted delivery of genes and antisense oligodeoxyribonucleotides via the folate receptor," Advanced Drug Delivery Reviews (2004) 56: 1193-1204.

Liu et al., "Lack of MK2 Inhibits Myofibroblast Formation and Exacerbates Pulmonary Fibrosis" Am. Respir. Cell. Mol. Biol. (2007) 34:507-517.

Decision of Reexamination dated Nov. 26, 2015 for Chinese Application No. 200980109550.4, filed Jan. 26, 2011.

Notification of Reexamination in Chinese Application No. 200980109550.4, dated Jul. 20, 2015.

Jun, Cheng, "Molecular Biology of Extracellular Matrix and Clinical Diseases", Beijing Medical University Press, pp. 243-250 (1999).

Office Action dated May 15, 2013 in Taiwanese Patent Application No. 098108655, filed Mar. 17, 2009.

Examination Report dated May 27, 2013 for Australian Patent Application No. 2009227445, filed on Mar. 17, 2009.

Nastruzzi, et al., "Liposome-associated retinoic acid increased in vitro antiproliferative effects on neoplastic cells" FEBS Letters (1990) 259(2):293-296.

Tabata, et al., "All-trans-retinoic acid prevents radiation- or bleomycin-induced pulmonary fibrosis", Am J Respir Crit Care Med. (Dec. 15, 2006) 174(12):1352-60.

(56) References Cited

OTHER PUBLICATIONS

Beljaars et al., "Albumin modified with mannosa 6-phosphate: a potential carrier for selective delivery of antifibrotic drugs to rat and human hepatic stellate cells," Hepatology, (1999):29(5):1486-1493.
Kang et al., "Mannose-6 phosphateyinsulin-like growth factor-II receptor is a receptor for retinoic acid," Proc. Natl. Acad. Sci. (1998) 95: 13671-13676.
Zhou, H., "A vitamin A-storing cell system," Foreign Medical Sciences (Section of Digestive Disease) (1986) 2: 104-106.
Notification of the 3$^{rd}$ Office Action dated Jun. 24, 2013, 2013 in Chinese Patent Application No. 200980109550.4, filed on Jan. 26, 2011.
Office Action dated Sep. 9, 2013 in Russian Patent Application No. 2010142226/15, filed Mar. 16, 2009.
Baybutt, et al., "Effects on cytokines and histology by treatment with the ACE inhibitor captopril and the antioxidant retinoic acid in the monocrotaline model of experimentally induced lung fibrosis." Curr Pharm Des. 2007; 13(13): 1327-33.
Torchilin, V. P. "Drug Targeting," European Journal of Pharmaceutical Sciences. (2000)11(2):81-91.
Marcucci, et al., "Active targeting with particulate drug carriers in tumor therapy: fundamentals and recent progress," Drug Discovery Today (2004) 9(5):219-228.
Office Action dated Dec. 18, 2013 in Chinse Patent Application No. 200980109550.4, filed Mar. 16, 2009.
Patent Examination Report No. 2 dated Feb. 4, 2014 in Australian Patent Application No. 2009227445, filed on Mar. 16, 2008.
Communication dated Mar. 10, 2014 in European Patent Application EP 09 722 829.0, filed on Mar. 16, 2009.
Communication dated Oct. 4, 2013 in European Patent Application EP 09 722 829.0, filed on Mar. 16, 2009.
Communication dated Apr. 30, 2013 in European Patent Application EP 09 722 829.0, filed on Mar. 16, 2009.
Extended European Search Report dated Feb. 24, 2011 in European Patent Application EP 09 722 829.0, filed on Mar. 16, 2009.
Decision of Rejection dated Apr. 22, 2014 for Chinese Application No. 200980109550.4, filed on Jan. 26, 2011.
Miao, et al., "Heat shock protein 47 and pulmonary fibrosis", *International J. Respiration* (2007) 27(22):1745-1747.
Baybutt et al., "Effects on cytokines and histology by treatment with the ACE inhibitor captopril and the antioxidant retinoic acid in the monocrotaline model of experimentally induced lung fibrosis," Curr Pharm Des. 2007; 13(13):1327-1333.
Notification on the Results of the Invention Patentability Verification dated Apr. 9, 2014 issued in Russian Patent Application No. 2010142226/15, filed on Mar. 16, 2009.
Office Action dated Jul. 29, 2014 issued in Japanese Patent Application No. 2013-170936, filed on Aug. 21, 2013.
An English translation of the claims as published on Apr. 11, 2014 in Japanese Application No. JP B 5517306.
Office Action dated Mar. 28, 2016 in Japanese Patent Application No. 2015-075906.
Examination Report Received in Indian Patent Application No. 1855/MUMNP/2010, dated Dec. 9, 2016.
Office Action Received in Chinese Patent Application No. 201610140450.X, dated Nov. 29, 2016.
Office Action Received in Taiwanese Patent Application No. 104112738, dated Aug. 18, 2016.
Stivala, et al., Effect of β-carotene on cell cycle progression of human fibroblasts, Carcinogenesis vol. 17, No. 11, pp. 2395-2401, 1996.
Landen et al., "Therapeutic EphA2 Gene Targeting In vivo Using Neutral Liposomal Small Interfering RNA Delivery," Cancer Res (2005) 65: (15), pp. 6910-6918.
Chinese Office Action dated Sep. 13, 2017 for Chinese Application No. 201610140450.X.
Chinese Office Action dated Feb. 14, 2018 for Chinese Application No. 201610141000.2.
Decision of Rejection dated Mar. 7, 2018 for Chinese Application No. 201610140450.X.
Extended European Search Report dated Apr. 11, 2016 in European Patent Application No. 15202384.2-1466.
Tabata Chihura "All trans-Retinoic acid prevents radiation- or bleomycin-induced pulmonary fibrosis" American Journal of Respiratory and Critical Care Medicine, vol. 174 No. 12 Dec. 2006 1352-1360.

\* cited by examiner

THERAPEUTIC AGENT FOR FIBROID LUNG

SEQUENCE LISTING

The present application is being filed along with a Sequence Listing in electronic format. The Sequence Listing is provided as a file entitled KUZU1_002C3.TXT, created Oct. 8, 2015, which is 1.96 KB in size. The information in the electronic format of the Sequence Listing is incorporated herein by reference in its entirety.

BACKGROUND OF THE INVENTION

Any and all applications for which a foreign or domestic priority claim is identified in the Application Data Sheet as filed with the present application are hereby incorporated by reference under 37 CFR 1.57.

Field of the Invention

The present invention relates to a substance delivery carrier targeted at extracellular matrix-producing cells in the lung, and a therapeutic agent for pulmonary fibrosis and a method for treating pulmonary fibrosis utilizing the carrier.

Description of the Related Art

Pulmonary fibrosis is a disease characterized by diffuse fibroplasia of the alveolar walls, and its main symptoms include dry cough and dyspnea on exertion. In a restricted sense, it refers to end-stage disease states of interstitial pneumonia; while in a broad sense, it means a co-existing state of pulmonary fibrosis in a restricted sense with interstitial pneumonia. Any interstitial pneumonia can cause pulmonary fibrosis. Interstitial pneumonia is a generic term for the diseases that induce inflammation in interstices of the lung (including alveolar septum in a restricted sense, and intralobular interstice and the vicinity of pleural membrane in a broad sense); it includes those induced by a specific cause such as infection, collagen disease, radiation, drug, and dust, and those without any known cause, i.e., idiopathic interstitial pneumonia. Idiopathic interstitial pneumonia is further classified as follows based on the findings of video-assisted thoracoscopic surgery (VATS) and high-resolution computer tomography (HRCT): idiopathic pulmonary fibrosis (IPF), nonspecific interstitial pneumonia (NSIP), acute interstitial pneumonia (AIP), cryptogenic organizing pneumonia (COP), respiratory bronchiolitis-associated interstitial lung disease (RB-ILD), desquamative interstitial pneumonia (DIP), lymphoid interstitial pneumonia (LIP), etc. Many of the interstitial pneumonia with specified causes are cured by elimination of the causes and administration of anti-inflammatory agents such as steroid drugs. However, regarding idiopathic interstitial pneumonia, there is no radical treatment method to date, and only treatments such as administration of steroid drugs, azathioprine and cyclophosphamide during exacerbation of symptoms, and oxygen therapy during development of hypoxemia are performed; accordingly, there are many dead cases in which idiopathic interstitial pneumonia progresses into pulmonary fibrosis. Therefore, the average survival period after establishment of diagnosis of idiopathic interstitial pneumonia is as short as 2.5-5 years, and this disease is designated as one of the specific diseases in Japan.

Under such circumstances, much research effort has been made to the development of therapeutic agents for pulmonary fibrosis. As a result, pharmaceutical agents such as colchicine, D-penicillamine, pirfenidone (5-methyl-1-phenyl-2-[1H]-pyridone), interferon-β1a, relaxin, lovastatin, beractant, N-acetylcysteine, keratinocyte growth factor, captopril (Non Patent Literature 1), hepatocyte growth factor (Patent Literature 1), Rho-kinase inhibitor (Patent Literature 2), thrombomodulin-like protein (Patent Literature 3), bilirubin (Patent Literature 4), PPARγ (peroxisome proliferator-activated receptor gamma) activator (Patent Literature 5), imatinib (Patent Literature 6), interferon-γ (Patent Literature 7) have been reported to show some effectiveness in animal models of pulmonary fibrosis or clinical trials. However, none of these agents is not yet satisfactory, and further development of the therapeutic agents for pulmonary fibrosis has been awaited.

CITATION LIST

Patent Literature 1: JP A No. 8-268906
Patent Literature 2: WO 00/57913
Patent Literature 3: JP A No. 2002-371006
Patent Literature 4: JP A No. 2003-119138
Patent Literature 5: JP A No. 2005-513031
Patent Literature 6: JP A No. 2005-531628
Patent Literature 7: JP A No. 2006-502153
Patent Literature 8: WO 2006/068232
Non Patent Literature 1: Ann Intern Med. 2001; 134(2): 136-51

SUMMARY OF INVENTION

Problems to be Solved by the Invention

An object of the present invention is to provide a carrier that can deliver a substance such as drugs specifically to extracellular matrix-producing cells in the lung, as well as a therapeutic agent for pulmonary fibrosis and a method for treating pulmonary fibrosis utilizing said carrier.

Means for Solving the Problems

The inventors of the present invention have searched for novel therapeutic agents for pulmonary fibrosis, and found that the administration of a composition in which a carrier comprising a retinoid carries an inhibitor for the production of extracellular matrix can effectively treat pulmonary fibrosis; then the inventors have completed this invention.

While it has been known that a carrier comprising vitamin A can deliver a drug to stellate cells that store vitamin A (refer to Patent Literature 8), the relationship with pulmonary fibrosis has been completely unknown to date.

Namely, the present invention relates to the following:

(1) A substance delivery carrier to an extracellularmatrix-producing cell in the lung, comprising a retinoid as a targeting agent.
(2) The carrier according to the above (1), wherein the retinoid derivative comprises retinol.
(3) The carrier according to the above (1) or (2), wherein the retinoid content is 0.2-20 wt % of the entire carrier.
(4) The carrier according to any one of the above (1) to (3), wherein the carrier has a form of liposome, and the molar ratio of the retinoid to the lipid contained in the liposome is 8:1-1:4.
(5) A composition for treating pulmonary fibrosis, comprising the carrier according to any one of the above (1) to (4) and a drug that controls the activity or growth of extracellular matrix-producing cells in the lung.
(6) The composition according to the above (5), wherein the drug that controls the activity or growth of extracellular matrix-producing cells in the lung is selected from the group consisting of an agent for inhibiting activity or production of a bioactive substance selected from the group consisting of gelatinase A, gelatinase B and angiotensinogen, an inhibitor of cell activity, a growth inhibitor, an apoptosis-inducing agent, as well as an siRNA (small interfering RNA), a ribozyme, an anti-sense nucleic acid, and a DNA/RNA chimeric polynucleotide which target at least one of extracellular matrix constituent molecules or molecules involved in the production or secretion of said extracellular matrix constituent molecules, and a vector that expresses said siRNA, ribozyme, anti-sense nucleic acid, and DNA/RNA chimeric polynucleotide.

(7) The composition according to the above (6), wherein the molecule involved in the production or secretion of the extracellular matrix constituent molecules is HSP (heat shock protein) 47.

(8) The composition according to any one of the above (5) to (7), wherein the drug and the carrier are mixed at a place of medical treatment or in its vicinity.

(9) A kit for preparing the composition according to any one of the above (5) to (8), wherein the kit comprises one or more containers comprising singly or in combination a drug for inhibiting activity or growth of extracellular matrix-producing cells in the lung, a retinoid, and if necessary, a carrier-constituent substance other than retinoid.

EFFECTS OF THE INVENTION

While the exact mechanism of action of the composition for treating pulmonary fibrosis of the present invention has not yet been completely clarified, the mechanism is considered as follows: with the composition, retinoid functions as a targeting agent to extracellular matrix-producing cells in the lung such as fibroblasts and myofibroblasts, and the retinoid delivers an active ingredient such as pharmaceutical agents that control activity or growth of extracellular matrix-producing cells in the lung to such cells, thereby exhibiting the effect against pulmonary fibrosis.

Accordingly, since active ingredients can be efficiently delivered to action sites, and further to targeted cells by using the carrier of the present invention, the treatment, suppression of progression, and prevention of onset of pulmonary fibrosis, in particular idiopathic interstitial pneumonia the treatment of which has been difficult to date are made possible; thus, the inventive carrier significantly contributes to the human medicine and veterinary medicine.

Moreover, the carrier of the present invention can be combined with any pharmaceutical drugs (for example, existing therapeutic agents for pulmonary fibrosis) to increase their action efficiency; therefore, it is also advantageous as its application range in terms of formulation is broad, facilitating the production of effective therapeutic agents.

DESCRIPTION OF EMBODIMENTS

In the present invention, the extracellular matrix-producing cells in the lung are not particularly limited as long as they are cells present in the lung and having a capability of producing extracellular matrix, and they include, for example, fibroblasts and myofibroblasts present in the lung. Fibroblasts present in the lung include, for example, vascular adventitial fibroblasts and bronchiolar adventitial fibroblasts, etc. Myofibroblasts present in the lung may include not only those derived from such fibroblasts present in the lung, but also those derived from fibroblasts in the circulating blood and those transformed from endothelial cells by endothelial mesenchymal transdifferentiation. Myofibroblasts are characterized by expression of α-smooth muscle actin (α-SMA). The myofibroblasts in the present invention are those identified, e.g., by immunostaining using detectably-labeled anti-α-SMA antibodies. In addition, while fibroblasts express vimentin that is characteristic to mesenchymal cells, they do not express α-SMA; therefore, fibroblasts can be identified by double-staining with vimentin and α-SMA.

The retinoid of the present invention is not particularly limited as long as it promotes delivery of a substance to extracellular matrix-producing cells in the lung, and examples thereof include retinoid derivatives such as retinol (vitamin A), etretinate, tretinoin, isotretinoin, adapalene, acitretine, tazarotene, and retinol palmitate, as well as vitamin A analogues such as fenretinide (4-HPR, 4-hydroxyphenylretinamide) and bexarotene.

The retinoid of the present invention is that which promotes specific delivery of a substance to extracellular matrix-producing cells in the lung. The mechanism of the promotion of substance delivery by retinoid has not yet been completely clarified; however, the following mechanism is considered: for example, a retinoid which has specifically bound to a retinol-binding protein (RBP) is taken into an extracellular matrix-producing cell in the lung through a certain receptor present on the surface of this cell.

A retinoid is a member of the class of compounds having a skeleton in which four isoprenoid units are bonded in a head-to-tail manner (see G. P. Moss, "Biochemical Nomenclature and Related Documents," 2nd Ed. Portland Press, pp. 247-251 (1992)). Vitamin A is a generic descriptor for a retinoid that qualitatively shows the biological activity of retinol. Retinoid that can be used in the present invention are not particularly limited, and examples thereof include retinoid derivatives such as retinol, retinal, retinoic acid, an ester of retinol and a fatty acid, an ester of an aliphatic alcohol and retinoic acid, etretinate, tretinoin, isotretinoin, adapalene, acitretine, tazarotene and retinol palmitate, and vitamin A analogues such as fenretinide (4-HPR) and bexarotene.

Of these, retinol, retinal, retinoic acid, an ester of retinol and a fatty acid (such as retinyl acetate, retinyl palmitate, retinyl stearate and retinyl laurate) and an ester of an aliphatic alcohol and retinoic acid (such as ethyl retinoate)

are preferable from the viewpoint of efficiency of specific delivery of a substance to extracellular matrix-producing cells in the lung.

All retinoid isomers, such as cis-trans, are included in the scope of the present invention. The retinoid may be substituted with one or more substituents. The retinoid in the present invention includes a retinoid in an isolated state as well as in a solution or mixture state with a medium that can dissolve or retain the retinoid.

The carrier of the present invention may be formed from the retinoid on its own or may be formed by making the retinoid bind to or enclosed in a carrier constituent component other than the retinoid. Therefore, the carrier of the present invention may comprise a carrier constituent component other than the retinoid. Such a component is not particularly limited, and any component known in the medicinal and pharmaceutical fields may be used, but those that can enclose retinoid or can bind thereto are preferable. Examples of such a component include a lipid, for example, a phospholipid such as glycerophospholipid, a sphingolipid such as sphingomyelin, a sterol such as cholesterol, a vegetable oil such as soybean oil or poppy seed oil, a mineral oil, and a lecithin such as egg-yolk lecithin, but the examples are not limited thereto. Among them, those that can form a liposome are preferable, for example, a natural phospholipid such as lecithin, a semisynthetic phospholipid such as dimyristoylphosphatidylcholine (DMPC), dipalmitoylphosphatidylcholine (DPPC), or distearoylphosphatidylcholine (DSPC), and dioleylphosphatidylethanolamine (DOPE), dilauroylphosphatidylcholine (DLPC), and cholesterol.

A particularly preferred component is a component that can avoid capture by the reticuloendothelial system, and examples thereof include cationic lipids such as N-(α-trimethylammonioacetyl)-didodecyl-D-glutemate chloride (TMAG), N,N',N'',N'''-tetramethyl-N,N',N'',N'''-tetrapalmitylspermine (TMTPS), 2,3-dioleyloxy-N-[2(sperminecarboxamido)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyldimethylammonium chloride (DODAC), didodecylammonium bromide (DDAB) 1,2-dioleyloxy-3-trimethylammoniopropane (DOTAP), 3β-[N-(N',N'-dimethylaminoethane)carbamoyl]cholesterol (DC-Chol), 1,2-dimyristoyloxypropyl-3-dimethylhydroxyethylammonium bromide (DMRIE), and O,O'-ditetradecanoyl-N-(α-trimethylammonioacetyl)diethanolamine chloride (DC-6-14).

The binding of the retinoid to the carrier of the present invention or the enclosing of it therein is also possible by binding or enclosing the retinoid to or in a constituent component, other than the retinoid, of the carrier by a chemical and/or physical method. Alternatively, the binding or enclosing the retinoid to or in the carrier of the present invention can also be carried out by mixing the retinoid and a constituent component, other than the retinoid, of the carrier when preparing the carrier. The amount of retinoid bound to or enclosed in the carrier of the present invention may be, as a weight ratio in the carrier constituent components, 0.01% to 100%, preferably 0.2% to 20%, and more preferably 1% to 5%. The binding or enclosing of retinoid to or in the carrier may be performed before a drug, etc. is carried on the carrier, may be performed by simultaneously mixing the carrier, a retinoid derivative and a drug, etc., or may be performed by mixing a retinoid derivative with a carrier on which a drug, etc. is already carried. Therefore, the present invention also relates to a process for producing a formulation specific to extracellular matrix-producing cells in the lung, the process including a step of binding a retinoid to any existing drug binding carrier or drug encapsulating carrier, for example, a liposomal formulation such as DaunoXome®, Doxil, Caelyx®, or Myocet®.

The form of the carrier of the present invention may be any form as long as a desired substance or matter can be transported to a target extracellular matrix-producing cell in the lung, and although not limited thereto, examples thereof include a macromolecular micelle, a liposome, an emulsion, microspheres, and nanospheres. In the present invention, from the viewpoint of high delivery efficiency, wide selection of substances to be delivered, and ease of making a formulation, etc., a liposomal form is preferable among the forms, and a cationic liposome that includes a cationic lipid is particularly preferable. In the case that the carrier is a liposomal form, the molar ratio of the retinoid to liposome constituent components other than the retinoid is, considering the efficiency of retinoid's binding to or enclosing in the carrier, preferably 8:1 to 1:4, more preferably 4:1 to 1:2, yet more preferably 3:1 to 1:1, and particularly preferably 2:1.

The carrier of the present invention may contain a substance to be transported within its interior, maybe attached to the exterior of a substance to be transported, or may be mixed with a substance to be transported, as long as retinoid contained therein is present in such a form that it can function as a targeting agent. "Function as a targeting agent" referred to here means that the carrier containing retinoid reaches and/or is taken up by the target cell, i.e., extracellular matrix-producing cells in the lung, more rapidly and/or in a larger quantity than with a carrier not containing retinoid, and this may easily be confirmed by, for example, adding a labeled or label-containing carrier to a culture of target cells, and analyzing the sites where the label is present after a predetermined period of time. Structurally, this requirement can be satisfied, for example, if retinoid is at least partially exposed to the exterior of a formulation containing the carrier at the latest by the time it reaches the target cell. Whether or not the retinoid is exposed at the exterior of a formulation can be evaluated by contacting the formulation to a substance that specifically binds to retinoid, such as a retinol-binding protein (RBP), and evaluating the binding to the formulation.

The substance or matter that is delivered by the present carrier is not particularly limited, and it preferably has a size such that it can physically move within the body of a living being from an administration site to a lesion site where a target cell is present. Therefore, the carrier of the present invention can transport not only a substance such as an atom, a molecule, a compound, a protein, or a nucleic acid, but also a matter such as a vector, a virus particle, a cell, a drug-releasing system formed from one or more elements, or a micromachine. The above substance or matter preferably has the property of having some influence on a target cell, and examples thereof include those that label a target cell and those that control (e.g. increase or suppress) the activity or growth of a target cell.

Therefore, in one embodiment of the present invention, the substance that the carrier delivers is "a drug controlling the activity or growth of an extracellular matrix-producing cell in the lung". The activity of an extracellular matrix-producing cell in the lung referred to here indicates various activities such as secretion, uptake, migration, etc. exhibited by an extracellular matrix-producing cell in the lung, and in the present invention among them it typically means, in particular, activities involved in the onset, progression, and/or recurrence of pulmonary fibrosis. Examples of such activities include, but are not limited to, production/secretion of a bioactive substance such as gelatinase A and gelatinase B (MMP (matrix metalloproteinase) 2 and MMP 9, respectively) and angiotensinogen, etc., and an extracellular matrix component such as collagen, proteoglycan, tenascin, fibronectin, thrombospondin, osteopontin, osteonectin, and elastin.

Therefore, the drug controlling the activity or growth of an extracellular matrix-producing cell in the lung may be any drug that directly or indirectly suppresses the physical, chemical, and/or physiological actions, etc. of said cell related to the onset, progression, and/or recurrence of pulmonary fibrosis, and while not being limited thereto, it includes the following: drugs inhibiting the activity or production of the above bioactive substances, MMP inhibitors such as batimastat, and antibodies and antibody fragments that neutralize the above bioactive substances, and substances that suppress expression of the above bioactive substances, such as an siRNA, a ribozyme, an antisense nucleic acid (including RNA, DNA, PNA (peptide nucleic acid), or a composite thereof), and substances that have a dominant negative effect such as a dominant negative mutant, or a vector expressing the same, drugs suppressing the production and secretion of the above extracellular matrix component, etc., for example, substances that suppress expression of the extracellular matrix component, such as an siRNA, a ribozyme, an antisense nucleic acid (including RNA, DNA, PNA, or a composite thereof), and substances that have a dominant negative effect such as a dominant negative mutant, or a vector expressing the same, inhibitors of cell activity such as a sodium channel blocker, cell-growth inhibitors, for example alkylating agents (such as ifosfamide, nimustine, cyclophosphamide, dacarbazine, melphalan, and ranimustine), antitumor antibiotics (such as idarubicin, epirubicin, daunorubicin, doxorubicin, pirarubicin, bleomycin, peplomycin, mitoxantrone, and mitomycin C), antimetabolites (such as gemcitabine, enocitabine, cytarabine, tegafur/uracil, a tegafur/gimeracil/oteracil potassium mixture, doxifluridine, hydroxycarbamide, fluorouracil, methotrexate, and mercaptopurine), alkaloids such as etoposide, irinotecan, vinorelbine, docetaxel hydrate, paclitaxel, vincristine, vindesine, and vinblastine, and platinum complexes such as carboplatin, cisplatin, and nedaplatin, and apoptosis inducers such as compound 861, gliotoxin, lovastatin, and Beractant. Furthermore, the "drug controlling the activity or growth of an extracellular matrix-producing cell in the lung" in the present invention may be any drug that directly or indirectly promotes the physical, chemical, and/or physiological actions, etc. of an extracellular matrix-producing cell In the lung directly or indirectly related to the suppression of onset, progression, and/or recurrence of pulmonary fibrosis.

The substance delivered by the carrier of the invention include, without limitation, drugs other than those mentioned above and which suppress the onset, progression, and/or recurrence of pulmonary fibrosis, and examples include, but are not limited to, colchicine, D-penicillamine, pirfenidone (5-methyl-1-phenyl-2-[1H]-pyridone), interferon-β1a, relaxin, N-acetylcysteine, keratinocyte growth factor, captopril, hepatocyte growth factor, Rho kinase inhibitor, thrombomodulin-like protein, bilirubin, PPARγ activator, imatinib, interferon-γ, and TGFβ receptor kinase inhibitor.

The substance or matter delivered by the carrier of the present invention mayor may not be labeled. Labeling enables monitoring of the success or failure of transport, increases and decreases testing/research level. A label may be selected from any label known to a person skilled in the art such as, for example, any radioisotope, magnetic material, substance that binds to a labeling substance matrix-producing cell in the lung" or "for the delivery to an extracellular matrix-producing cell in the lung" means that it is suitable to use to extracellular matrix-producing cells as a target, and this includes it being possible to deliver a substance to this cell, more rapidly, efficiently, and/or in a larger quantity than to other cells, for example, normal cells. For example, the carrier of the present invention can deliver a substance to an extracellular matrix-producing cell in the lung at a rate and/or efficiency of 1.1 times or more, 1.2 times or more, 1.3 times or more, 1.5 times or more, 2 times or more, or even 3 times or more compared with other cells.

The present invention also relates to a composition for controlling the activity or growth of an extracellular matrix-producing cell in the lung, or for treating pulmonary fibrosis, that comprises the carrier, and the drug controlling the activity or growth of an extracellular matrix-producing cell in the lung, and to a use of the carrier in the production of such compositions.

In the present invention, pulmonary fibrosis includes not only pulmonary fibrosis in a restricted sense, but also pulmonary fibrosis in a broad sense that includes co-existence of interstitial pneumonia. The pulmonary fibrosis of the present invention can be interstitial pneumonia associated with viral pneumonia, fungal pneumonia, mycoplasmal pneumonia, etc., interstitial pneumonia associated with collagen disease such as rheumatoid arthritis, systemic scleroderma, dermatomyositis, polymyositis, mixed connective-tissues disease (MCTD), etc., interstitial pneumonia associated with radiation exposure, drug-induced interstitial pneumonia caused by anticancer agents such as bleomycin, herbal medicines such as Sho-sai-ko-to, interferon, antibiotics, paraquat, etc., and idiopathic interstitial pneumonia such as idiopathic pulmonary fibrosis, nonspecific interstitial pneumonia, acute interstitial pneumonia, cryptogenic organizing pneumonia, respiratory bronchiolitis-associated interstitial lung disease, desquamative interstitial pneumonia, lymphoid interstitial pneumonia, etc., and accordingly, it also includes chronic states of such interstitial pneumonia. The pulmonary fibrosis of the present invention preferably includes chronic states of drug-induced interstitial pneumonia and idiopathic interstitial pneumonia.

In the composition of the present invention, as long as the retinoid contained in the carrier is present in a mode that functions as a targeting agent, the carrier may contain a substance to be delivered within its interior, may be attached to the exterior of a substance to be delivered, or may be mixed with a substance to be delivered. Therefore, depending on the administration route and the manner in which the drug is released, etc., the composition may be covered with an appropriate material such as, for example, an enteric coating or a material that disintegrates over time, or may be incorporated into an appropriate drug release system.

The composition of the present invention may be administered via various routes including both oral and parenteral routes, and examples thereof include, but are not limited to, oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes, and it may be formulated into a dosage form suitable for each administration route. Such a dosage form and formulation method may be selected as appropriate from any known dosage forms and methods (see e.g. Hyojun Yakuzaigaku (Standard Pharmaceutics), Ed. by Yoshiteru Watanabe et al., Nankodo, 2003).

Examples of dosage forms suitable for oral administration include, but are not limited to, powder, granule, tablet, capsule, liquid, suspension, emulsion, gel, and syrup, and examples of the dosage form suitable for parenteral administration include injections such as an injectable solution, an injectable suspension, an injectable emulsion, and an injection to be prepared immediately before use. Formulations for parenteral administration may be a form such as an aqueous or nonaqueous isotonic sterile solution or suspension.

The carrier or the composition of the present invention may be supplied in any form, but from the viewpoint of storage stability, it is preferably provided in a form that can be prepared immediately before use, for example in a form that allows a doctor and/or a pharmacist, a nurse, another paramedic, etc. to prepare it at the place of treatment or in the vicinity thereof. In this case, the carrier or the composition of the present invention is provided as one or more containers containing at least one essential constituent element therefor, and it is prepared prior to use, for example, within 24 hours prior to use, immediately prior to use. When preparing, a reagent, a solvent, preparation equipment, etc. that are normally available in a place of preparation may be used as appropriate.

The present invention therefore also relates to a preparation kit for the carrier or the composition, the kit including one or more containers containing singly or in combination a retinoid, and/or a substance to be delivered, and/or a carrier-constituting substance other than the retinoid, and also to a constituent element necessary for the carrier or the composition provided in the form of such a kit. The kit of the present invention may contain, in addition to the above, instructions, an electronic recording medium such as a CD or DVD related to a process for preparing the carrier and the composition of the present invention, or an administration method, etc. Furthermore, the kit of the present invention may include all of the constituent elements for completing the carrier or the composition of the present invention, but need not always include all of the constituent elements. Therefore, the kit of the present invention need not include a reagent or a solvent that is normally available at a place of medical treatment, an experimental facility, etc. such as, for example, sterile water, physiological saline, or a glucose solution.

The present invention further relates to a method for controlling the activity or growth of an extracellular matrix-producing cell in the lung, or a method for treating pulmonary fibrosis, the method including administering an effective amount of the composition to a subject in need thereof. The effective amount referred to here is, in a method for treating pulmonary fibrosis, pulmonary fibrosis, alleviates its symptoms, or delays or stops its progression, and is preferably an amount that prevents the onset or recurrence of pulmonary fibrosis or cures it. It is also preferably an amount that does not cause an adverse effect that exceeds the benefit from administration. Such an amount may be determined as appropriate by an in vitro test using cultured cells or by a test in a model animal such as a mouse, a rat, a dog, or a pig, and such test methods are well known to a person skilled in the art. Moreover, the dose of the retinoid contained in the carrier and the dose of the drug used in the method of the present invention are known to a person skilled in the art, or maybe determined as appropriate by the above-mentioned test, etc.

In the method of the present invention, the specific dose of the composition administered may be determined while taking into consideration various conditions with respect to a subject in need of the treatment, such as the severity of symptoms, general health condition of the subject, age, body weight, gender of the subject, diet, the timing and frequency of administration, a medicine used in combination, response to the treatment, compliance with the treatment, etc.

As the administration route, there are various routes including both oral and parenteral routes, and examples thereof include oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes.

The frequency of administration depends on the properties of the composition used and the above-mentioned conditions of the subject, and may be a plurality of times per day (that is, 2, 3, 4, 5, or more times per day), once a day, every few days (that is, every 2, 3, 4, 5, 6, or 7 days, etc.), a few times per week (e.g. 2, 3, 4 times, etc. per week), every other week, or every few weeks (that is, every 2, 3, 4 weeks, etc.).

In the method of the present invention, the term "subject" means any living individual, preferably an animal, more preferably a mammal, and yet more preferably a human individual. In the present invention, the subject may be healthy or affected by some disorder, and when treatment of pulmonary fibrosis is intended, it typically means a subject affected by interstitial pneumonia or pulmonary fibrosis, or having a risk of being affected by them. For example, when prevention of pulmonary fibrosis is intended, typical examples include, but are not limited to, a subject affected by interstitial pneumonia, in particular by idiopathic interstitial pneumonia.

Furthermore, the term "treatment" includes all types of medically acceptable preventive and/or therapeutic intervention for the purpose of the cure, temporary remission, or prevention of a disorder, etc. For example, the term "treatment" includes medically acceptable intervention of various purposes, including delaying or stopping the progression of pulmonary fibrosis, regression or disappearance of lesions, prevention of onset and prevention of recurrence of pulmonary fibrosis.

The present invention also relates to a method for delivering a drug to an extracellular matrix-producing cell in the lung, utilizing the above carrier. This method includes, but is not limited the carrier, and a step of administering or adding the carrier having the substance to be delivered carried thereon to a living being or a medium, for example a culture medium, containing an extracellular matrix-producing cell in the lung. These steps may be achieved as appropriate in accordance with any known method or a method described In the present specification, etc. The above delivery method may be combined with another delivery method, for example, another delivery method targeted at the lung. Moreover, the above method includes a mode carried out in vitro and a mode in which an extracellular matrix-producing cell in the lung inside the body is targeted.

EXAMPLES

The present invention is explained in detail by reference to specific examples below, but these specific examples are for illustrative purposes, and do not limit the scope of the present invention.

Example 1

Preparation of siRNA

Three types of siRNA targeted at gp46 (GenBank Accession No. M6924 6), which is a rat homologue of human HSP47, and a random siRNA control were purchased from Hokkaido System Science Co., Ltd. Each siRNA consists of 27 bases overhanging on the 3' side, and the sequences are as follows.

```
Sequence A:
                            (sense, SEQ ID NO: 1)
5'-GUUCCACCAUAAGAUGGUAGACAACAG-3, (antisense, SEQ ID NO: 2)
5'-GUUGUCUACCAUCUUAUGGUGGAACAU-3, Sequence B:
                            (sense, SEQ ID NO: 3)
5'-CCACAAGUUUUAUAUCCAAUCUAGCAG-3, (antisense, SEQ ID NO: 4)
5'-GCUAGAUUGGAUAUAAAACUUGUGGAU-3, (antisense, SEQ ID NO: 6)
5'-UGUCAAUGUAAUGUAAUGGCUCUAGAU-3, Random siRNA:
                            (sense, SEQ ID NO: 7)
5'-CGAUUCGCUAGACCGGCUUCAUUGCAG-3'

(antisense, SEQ ID NO: 8)
5'-GCAAUGAAGCCGGUCUAGCGAAUCGAU-3,
```

Furthermore, siRNA that was labeled on the 5' side with the fluorescent dye 6'-carboxyfluorescein (6-FAM) was also prepared.

Example 2

Preparation of siRNA-containing VA-bound Liposome

As a liposome, a cationic liposome containing DC-6-14, cholesterol, and DOPE at a molar ratio of 4:3:3 (Lipotrust, Hokkaido System Science Co., Ltd.) was used. 10 nmol of liposome and 20 nmol of vitamin A (VA: all-trans retinol, Sigma) were mixed in DMSO using a 1.5-mL tube, then dissolved in chloroform, evaporated once, and then suspended in PBS (phosphate buffered saline). Subsequently, the siRNA (10 μg/mL) obtained in Example 1 and the liposome suspension were mixed at a ratio of 1:1 (w/w). Free VA and siRNA contained In the liposome suspension thus obtained were removed by a micropartition system (SartorionVIVASPIN5000MWCOPES), thus giving an siRNA-containing VA-bound liposome (VA-lip-siRNA). The amount of VA added and the amount of VA contained in the purified liposome were measured by HPLC, and the proportion of VA bound to the liposome was examined; as a result, it was found that the majority of the VA (95.6±0.42%) was bound to the liposome. Furthermore, the efficiency of uptake of siRNA into the liposome was measured by RiboGreen assay (Molecular Probes), and it was as high as 94.4±3.0%. Here, in this formulation, VA was at least partially exposed on the surface of the formulation.

Example 3

Figure 1:
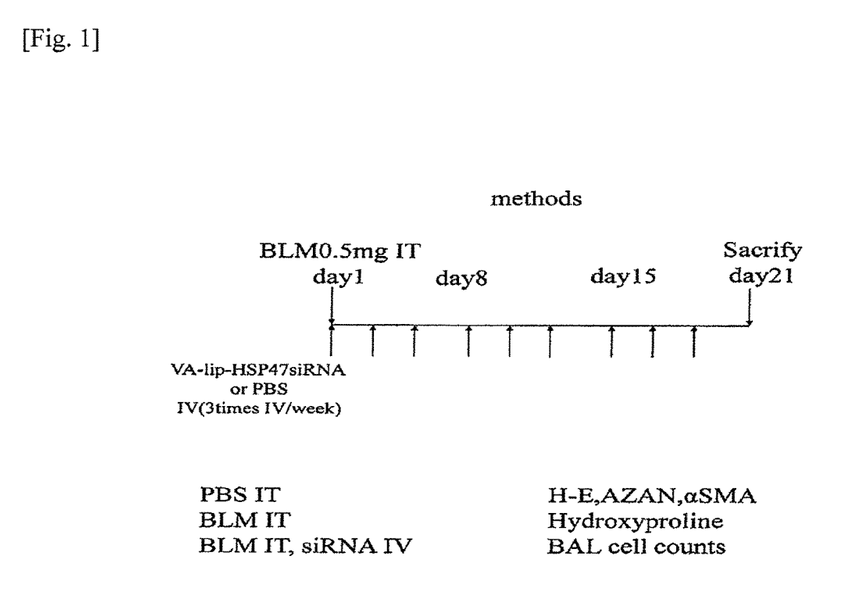
FIG. 1 is a schematic diagram showing induction of pulmonary fibrosis in rats and drug-administration schedule.

In Vivo Anti-pulmonary-fibrosis Activity of siRNA-containing VA-bound Liposome (1) Induction of Pulmonary Fibrosis and Administration of Drug Male S-D rats (6 rats/group, 4 weeks old, Charles River Laboratories Japan, Inc.) were administered once with 0.5 mg bleomycin (BLM) dissolved in 0.5 cc of physiological saline into the lung intratracheally by intratracheal cannulation under anesthesia, to produce a bleomycin pulmonary fibrosis model. With this method, a significant fibrosis occurs in the lung generally after approximately 3 weeks. The VA-lip-siRNA prepared in Example 2 (0.75 mg/kg as an amount of siRNA, 1 ml/kg in volume, i.e., 200 μl for a rat of 200 g) or PBS (1 ml/kg in volume) was administered to the rats via the tail vein, starting from the day of administration of bleomycin, at a frequency of 3 times/week. The rats were sacrificed 21 days after the bleomycin administration, and bronchoalveolar lavage (BAL) fluid was analyzed, hydroxyproline in the lung was quantified, and histological investigation of the lung tissue was performed (see FIG. 1). Student's t-test was used for the evaluation of statistically-significant difference.

(2) Analysis of BAL fluid

Figure 2:
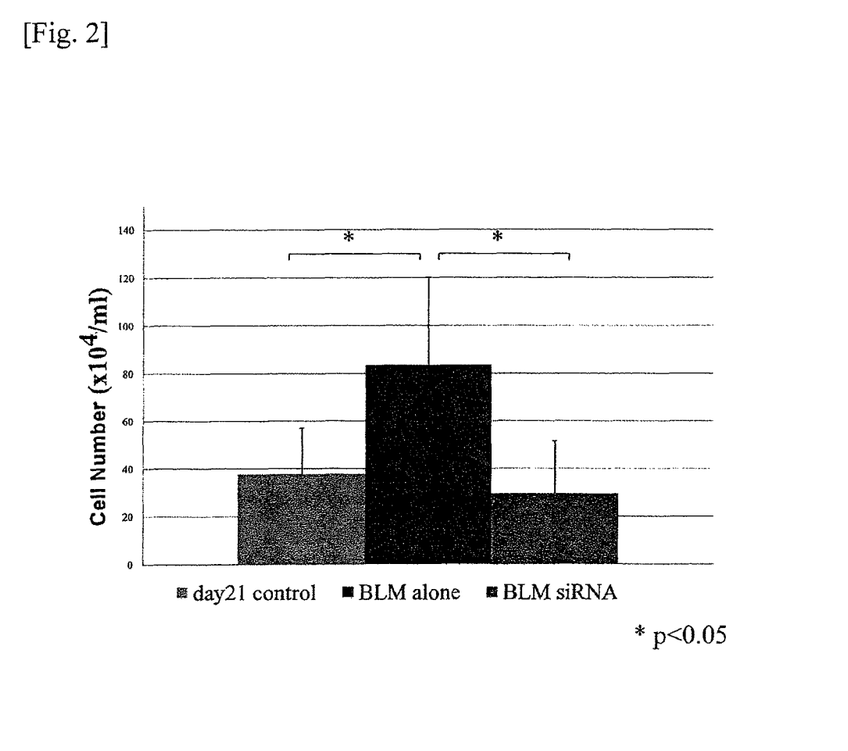
FIG. 2 is a graph showing the total number of cells in BAL liquid on day 21 after administration of bleomycin. "Control" means normal rats without administration of bleomycin.

Analysis of BAL was performed as follows. The rats were intraperitoneally administered with a lethal dose of pentobarbital sodium, their thorax was opened, then the trachea was exposed and a cannula was inserted into the trachea. Subsequently, 7 ml of physiological saline was injected into the lung via the tracheal cannula and the lavage fluid was collected. This process of injection and collection was repeated 5 times, and the collected lavage fluids were combined and centrifuged at 250×g for 10 min. The total number of cells was counted using a cytometer, and cell fraction count was performed using a May-Giemsa stained cytospin smear preparation. At least 200 cells were counted and classified into macrophage, eosinophil, neutrophil, and lymphocyte in accordance with general morphological criteria. Results of the total cell number count were shown in FIG. 2. This figure shows that the number of cells in the BAL fluid of the VA-lip-siRNA administration group (BLM siRNA) significantly decreased to the level similar to that of the normal control rat administered with PBS instead of bleomycin, compared to the PBS administration group (BLM alone); suggesting that inflammation has been improved.

(3) Quantification of Hydroxyproline in Lung Tissue

Figure 3:
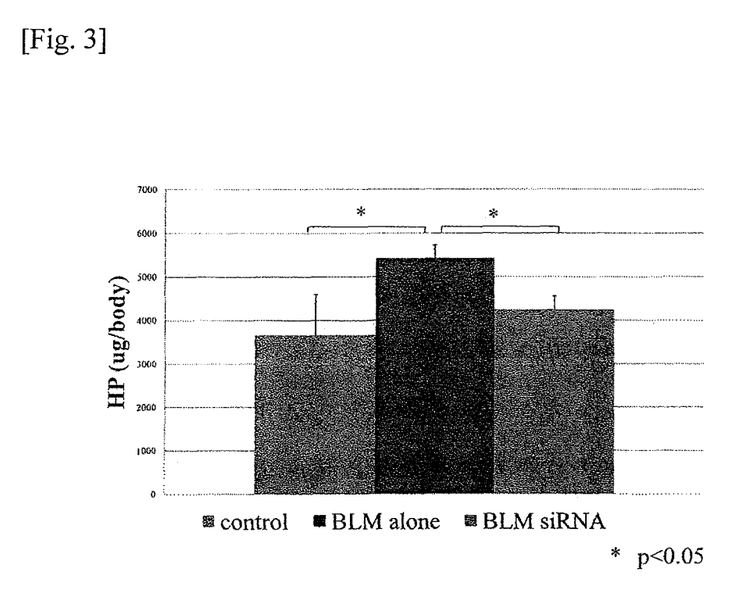
FIG. 3 is a graph showing the amount of hydroxyproline (HP) In the lung on day 21 after administration of bleomycin. "Control" means normal rats without administration of bleomycin.

The lung was removed from the rats after BAL, then one whole lung was homogenized using a polytron homogenizer, and the lung hydroxyproline was quantified using a method of Kivirikko, et al. (Kivirikko K I, et al. Analytical Biochemistry 1967; 19: 249-255). Namely, the lung tissue was homogenized in 6-N hydrochloric acid at 110° C. for 18 hr, and 25-μl aliquot was dried at 60° C. It was then dissolved in 1.2 ml of 50% isopropanol, incubated with acetate citrate, pH 6.0, and 200 ml of 0.56% chloramine-T solution at room temperature for 10 min, followed by an incubation at 50° C. for 90 min after the addition of 1 ml of Ehrlich solution; then absorbance at 560 nm was measured. Results shown in FIG. 3 indicate that the amount of lung hydroxyproline (μg) of the VA-lip-siRNA administration group (BLM siRNA) significantly decreased compared to that of the PBS administration group (BLM alone), suggesting that the fibrosis of the lung was significantly suppressed.

(4) Histological Investigation

Figure 4:
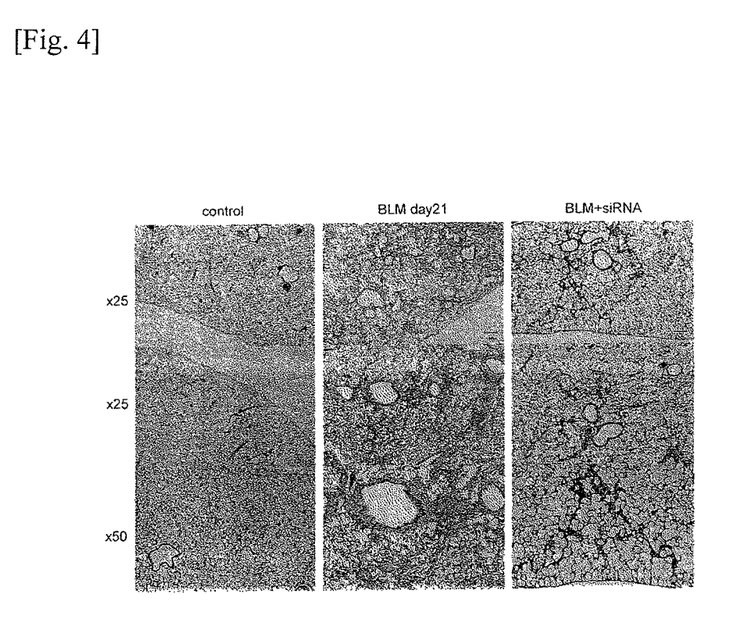
FIG. 4 shows photographs of HE-stained lung tissues on day 21 after administration of bleomycin.
Figure 5:
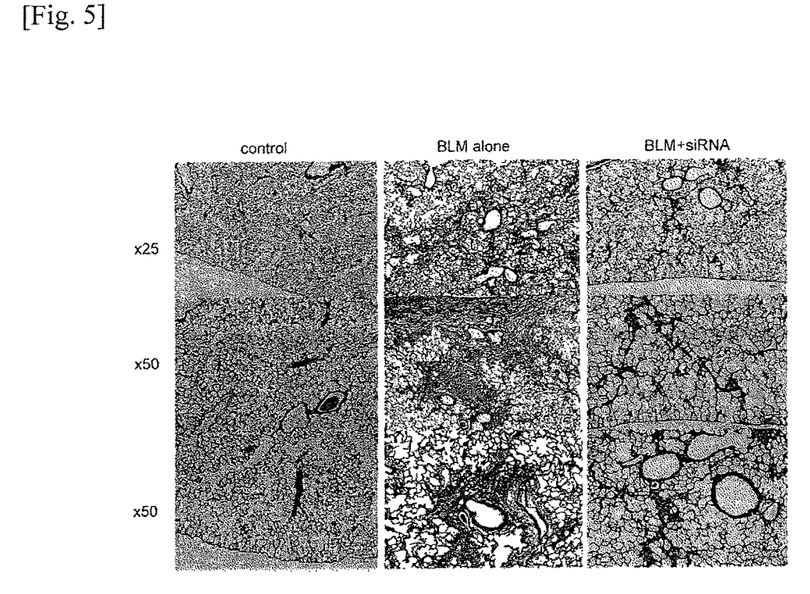
FIG. 5 shows photographs of Azan-stained lung tissues on day 21 after administration of bleomycin.
Figure 6:
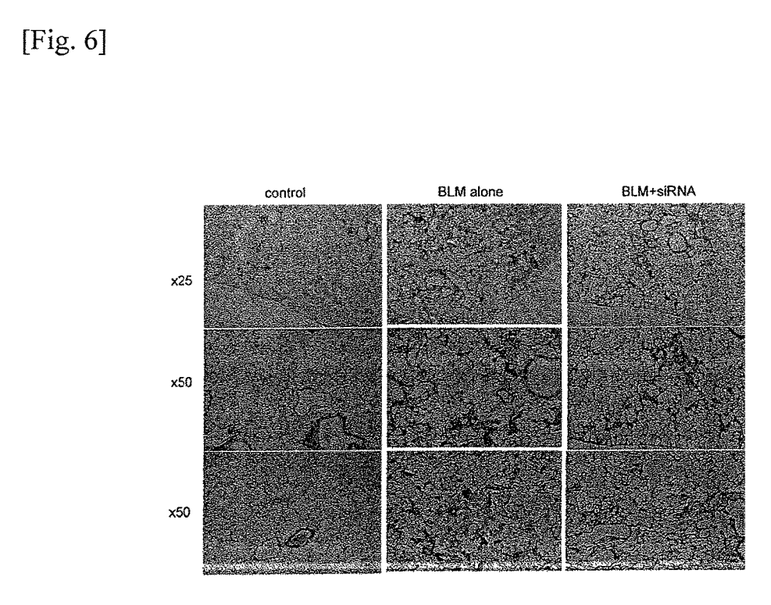
FIG. 6 shows photographs showing distribution of αSMA-positive cells in the lung tissues on day 21 after administration of bleomycin.

A part of the removed lung was formalin-fixed in accordance staining, azanstaining (azocarmine, anilineblueorangeGsolution), or immunostaining with anti-αSMA antibody. Regarding the immunostaining, after deparaffinization, samples were reacted with a mouse anti-αSMA antibody (Nichirei Corporation, clone 1A4) as a primary antibody, then with a peroxidase-labeled anti-mouse IgG as a secondary antibody, and developed with DAB. As shown by the results of HE staining in FIG. 4, in the PBS administration group (BLM day 21), findings characteristic to pulmonary fibrosis such as disappearance of pulmonary alveoli, bleeding images and interstitial hyperplasia were observed, whereas in the VA-lip-siRNA administration group (BLM+siRNA), fibrotic lesions were significantly improved. Similarly, as shown by the results of the azan staining in FIG. 5, in the PBS administration group (BLM alone), a noticeable fibrotic image characterized by enlargement of interstice due to a large quantity of blue-stained collagenous fibrils was observed, whereas in the VA-lip-siRNA administration group (BLM+siRNA), fibrosis were apparently suppressed. Moreover, as shown by the results of the αSMA staining in FIG. 6, while a large number of αSMA-positive cells having a brown color were observed in the interstice in the PBS administration group (BLM alone), the number of αSMA-positive cells significantly decreased in the VA-lip-siRNA administration group (BLM+siRNA).

Considering that siRNA basically acts in the cytoplasm, the above results indicate that the retinoid functioned as a targeting agent to extracellular matrix-producing cells in the lung, so that a drug is efficiently delivered to these cells, leading to a significant improvement in disease states of pulmonary fibrosis.

What is claimed is:

1. A method for treating pulmonary fibrosis, the method comprising administering an effective amount of a therapeutic composition to a human subject in need thereof, wherein the therapeutic composition comprises a substance delivery carrier comprising an amount of a retinoid that is effective to promote delivery of the substance to the extracellular matrix-producing cells in the lung, and a drug in an amount effective for controlling the activity or growth of the extracellular matrix-producing cells in the lung, wherein the substance delivery carrier has a form of a cationic liposome and the molar ratio of the retinoid to the lipid contained in the liposome is 8:1-1:4, and wherein the retinoid content is 0.2-20 wt % of the entire carrier, wherein the drug is selected from the group consisting of an siRNA which targets HSP47, a ribozyme which targets HSP47, an anti-sense nucleic acid which targets HSP47, a DNA/RNA chimeric polynucleotide which targets HSP47, a vector that expresses said siRNA, a vector that expresses said ribozyme, a vector that expresses said anti-sense nucleic acid, and a vector that expresses said DNA/RNA chimeric polynucleotide.

2. The method of claim 1, wherein the retinoid comprises retinol.

3. The method of claim 1, wherein the drug is an siRNA which targets HSP47.

4. The method of claim 1, wherein the drug is a ribozyme which targets HSP47.

5. The method of claim 1, wherein the drug is an anti-sense nucleic acid which targets HSP47.

6. The method of claim 1, wherein the drug is a DNA/RNA chimeric polynucleotide which targets HSP47.

* * * * *

UNITED STATES PATENT AND TRADEMARK OFFICE
CERTIFICATE OF CORRECTION

PATENT NO. : 10,098,953 B2
APPLICATION NO. : 14/883370
DATED : October 16, 2018
INVENTOR(S) : Yoshiro Niitsu It is certified that error appears in the above-identified patent and that said Letters Patent is hereby corrected as shown below:

In the Specification

Column 3 Line 65, Change "In" to --in--.

Column 4 Line 37, Change "acitretine," to --acitretin,--.

Column 4 Line 61, Change "acitretine," to --acitretin,--.

Column 5 Line 29-30, Change "dioleylphosphatidylethanolamine" to --dioleoylphosphatidylethanolamine--.

Column 5 Line 35, Change "glutemate" to --glutamate--.

Column 7 Line 49, Change "In" to --in--.

Column 7 Line 64, Change "mayor" to --may or--.

Column 10 Line 60, Change "In" to --in--.

Column 11 Line 57, Change "In" to --in--.

Column 12 Line 63, Change "Ehrilich" to --Ehrlich--.

Signed and Sealed this
Nineteenth Day of March, 2019

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 27
<212> TYPE: RNA
<213> ORGANISM: Artificial Sequence
<220> FEATURE:
<223> OTHER INFORMATION: Sense strand of gp46siRNAseqA

<400> SEQUENCE: 1
guuccaccau aagaugguag acaacag                                           27

<210> SEQ ID NO 2
<211> LENGTH: 27
<212> TYPE: RNA
<213> ORGANISM: Artificial Sequence
<220> FEATURE:
<223> OTHER INFORMATION: Antisense strand of gp46siRNAseqA

<400> SEQUENCE: 2
guugucuacc aucuuauggu ggaacau                                           27

<210> SEQ ID NO 3
<211> LENGTH: 27
<212> TYPE: RNA
<213> ORGANISM: Artificial Sequence
<220> FEATURE:
<223> OTHER INFORMATION: Sense strand of gp46siRNAseqB

<400> SEQUENCE: 3
ccacaaguuu uauauccaau cuagcag                                           27

<210> SEQ ID NO 4
<211> LENGTH: 27
<212> TYPE: RNA
<213> ORGANISM: Artificial Sequence
<220> FEATURE:
<223> OTHER INFORMATION: Antisense strand of gp46siRNAseqB

<400> SEQUENCE: 4
gcuagauugg auauaaaacu uguggau                                           27

<210> SEQ ID NO 5
<211> LENGTH: 27
<212> TYPE: RNA
<213> ORGANISM: Artificial Sequence
<220> FEATURE:
```

```
<223> OTHER INFORMATION: Sense strand of gp46siRNAseqC

<400> SEQUENCE: 5
cuagagccau uacauuacau ugacaag                                              27

<210> SEQ ID NO 6
<211> LENGTH: 27
<212> TYPE: RNA
<213> ORGANISM: Artificial Sequence
<220> FEATURE:
<223> OTHER INFORMATION: Antisense strand of gp46siRNAseqC

<400> SEQUENCE: 6
ugucaaugua auguaauggc ucuagau                                              27

<210> SEQ ID NO 7
<211> LENGTH: 27
<212> TYPE: RNA
<213> ORGANISM: Artificial Sequence
<220> FEATURE:
<223> OTHER INFORMATION: Sense strand of random siRNA

<400> SEQUENCE: 7
cgauucgcua gaccggcuuc auugcag                                              27

<210> SEQ ID NO 8
<211> LENGTH: 27
<212> TYPE: RNA
<213> ORGANISM: Artificial Sequence
<220> FEATURE:
<223> OTHER INFORMATION: Antisense strand of random siRNA

<400> SEQUENCE: 8
gcaaugaagc ggucuagcg aaucgau                                               27
```